US010028719B1

(12) United States Patent
Bernhardt et al.

(10) Patent No.: US 10,028,719 B1
(45) Date of Patent: Jul. 24, 2018

(54) ADJUSTING AN X-RAY PARAMETER OF AN X-RAY UNIT

(71) Applicant: Siemens Healthcare GmbH, Erlangen (DE)

(72) Inventors: Philipp Bernhardt, Forchheim (DE); Rudolf Leiblein, Weisendorf (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 0 days.

(21) Appl. No.: 15/856,160

(22) Filed: Dec. 28, 2017

(30) Foreign Application Priority Data

Jan. 17, 2017 (DE) ........................ 10 2017 200 677

(51) Int. Cl.
*A61B 6/00* (2006.01)
*G01N 23/00* (2006.01)
*G01N 23/20008* (2018.01)

(52) U.S. Cl.
CPC ............ *A61B 6/545* (2013.01); *A61B 6/5205* (2013.01); *G01N 23/20008* (2013.01); *G01N 2223/306* (2013.01)

(58) Field of Classification Search
CPC ...................................................... A61B 6/542
See application file for complete search history.

(56) References Cited

U.S. PATENT DOCUMENTS 5,617,462 A * 4/1997 Spratt ...................... H05G 1/30 378/108
2008/0075347 A1 * 3/2008 Ruhrnschopf ........ G06T 11/005 382/131
2008/0095313 A1 4/2008 Bernhardt
2011/0317806 A1 12/2011 Schmidt

FOREIGN PATENT DOCUMENTS

DE 102006045722 A1 4/2008
DE 102006046732 A1 4/2008
DE 102012200150 A1 7/2013
DE 1020140041176 B4 1/2015

OTHER PUBLICATIONS

German Office Action #102017200677.3 dated Oct. 25, 2017.
German Decision to Grant #10201720067.3 dated Dec. 18, 2017.

* cited by examiner

*Primary Examiner* — Dani Fox
(74) *Attorney, Agent, or Firm* — Harness, Dickey & Pierce, P.L.C.

(57) ABSTRACT

An X-ray projection of a region of examination and an associated X-ray parameter are received via an interface, the X-ray projection including X-ray intensities in a first pixel set. The X-ray parameter relates to at least one X-ray voltage from an X-ray source. Scattered radiation intensity is determined in a second pixel set, the second pixel set being a subset of the first pixel set. A first calculation of first exposure parameters in the second pixel set then occurs, each of the first exposure parameters in a pixel of the second pixel set being based on the X-ray intensity in the pixel and the scattered radiation intensity in the pixel. Furthermore, a second calculation of a scalar second exposure parameter occurs based on the first exposure parameters and an adjustment of the X-ray parameter is performed by comparing the scalar second exposure parameter with a reference value.

24 Claims, 3 Drawing Sheets

300
301
304
500
306
303
z
y
x
305
501
302
502.1 502.2 502.3

ADJUSTING AN X-RAY PARAMETER OF AN X-RAY UNIT

PRIORITY STATEMENT

The present application hereby claims priority under 35 U.S.C. § 119 to German patent application number DE 102017200677.3 filed Jan. 17, 2017, the entire contents of which are hereby incorporated herein by reference.

FIELD

At least one embodiment of the invention generally relates to a method for adjusting an X-ray parameter of an X-ray unit; a parameter adjusting unit; an X-ray unit including the parameter adjusting unit; a computer program product configured to perform the method and/or a computer readable storage medium configured to perform the method.

BACKGROUND

The use of X-rays is a widespread method for depicting the internal structure of objects, in particular in medical imaging or in non-destructive material testing. Herein, the object to be depicted is often very heterogeneous, i.e. there are regions of the object in which X-rays are absorbed weakly (in medical imaging, lung tissue for example) and simultaneously regions in which radiation is strongly absorbed (in medical imaging, bone regions for example). Therefore, depictions of the object have high dynamics in the registered X-ray intensities.

A method is known from the patent DE 10 2010 041 176 B4 for operating X-ray units with automatic lighting control. Herein, the aim of automatic lighting control is to achieve good image quality in the relevant regions of the image and simultaneously the lowest possible X-ray dose absorption by the object. Automatic lighting control is in particular used in fields of application in which multiple X-ray images of the same object are recorded, for example in fluoroscopy or the X-ray angiography. Herein, fluoroscopy (an equivalent term is "transillumination") is understood to mean the continuous recording of processes in an object, in particular in a human body, by way of X-rays. X-ray angiography is a typically time-resolved depiction of vessels by way of X-rays, wherein contrast medium is injected into the vessels.

The X-rays generated in known X-ray units are homogeneous, i.e. both strongly and weakly absorbent regions of the object to be depicted are irradiated with the same X-ray intensity. This represents an additional challenge for the lighting control.

However, the X-ray intensity registered in the X-ray detector is not the only factor influencing image quality. The signal-noise ratio, and hence the image quality, furthermore depend upon the content of scattered radiation. Scattered radiation generally has much lower X-ray dynamics than primary radiation. Therefore, regions with a strong X-ray absorption have a much higher content of scattered radiation than regions with low X-ray absorption.

SUMMARY

At least one embodiment of the present invention enables an improvement to the automatic lighting control of an X-ray unit.

At least one embodiment of the present invention is directed to a method; a parameter-control unit; an X-ray unit; a computer program product and/or a computer-readable storage medium.

The following example embodiment explain inventive solutions with respect to devices and methods. Features, advantages or alternative embodiments mentioned herein can also be transferred to the claimed subject matter and vice versa. In other words, the material claims (which are, for example, directed at a device) can also be developed with the features which are described or claimed in connection with a method. Herein, the corresponding functional features of the method are embodied by corresponding material modules.

At least one embodiment of the invention relates to a method for adjusting an X-ray parameter of an X-ray unit, wherein the X-ray unit comprises an X-ray source and an X-ray detector, the method comprising:

reception of an X-ray projection of a region of interest and an associated X-ray parameter via an interface, wherein the X-ray projection comprises X-ray intensities in a first pixel set, and wherein the X-ray parameter relates to at least one X-ray voltage from the X-ray source, determination of scattered radiation intensities in a second pixel set via a computing unit, wherein the second pixel set is a subset of the first pixel set, first calculation of first exposure parameters in the second pixel set via the computing unit, wherein each of the first exposure parameters in a pixel of the second pixel set is based on the X-ray intensity in the pixel and the scattered radiation intensity in the pixel, second calculation of a scalar second exposure parameter based on the first exposure parameters via the computing unit, and adjustment of the X-ray parameter by comparing the scalar second exposure parameter with a reference value via the computing unit.

At least one embodiment of the invention furthermore relates to a parameter-adjusting unit for adjusting an X-ray parameter of an X-ray unit, wherein the X-ray unit comprises an X-ray source and an X-ray detector comprising the following units:

- an interface embodied for the reception of an X-ray projection of a region of interest and an associated X-ray parameter, wherein the X-ray projection comprises X-ray intensities in a first pixel set and wherein the X-ray parameter relates to at least one X-ray voltage from the X-ray source,
- a computing unit embodied for the determination of scattered radiation intensities in a second pixel set, wherein the second pixel set is a subset of the first pixel set, furthermore embodied for the first calculation of first exposure parameters in the second pixel set, wherein each of the first exposure parameters in a pixel of the second pixel set is based on the X-ray intensity in the pixel and the scattered radiation intensity in the pixel, furthermore embodied for the second calculation of a scalar second exposure parameter based on the first exposure parameters, furthermore embodied for the adjustment of the X-ray parameter by comparing the scalar second exposure parameter with a reference value.

At least one embodiment of the invention furthermore relates an X-ray unit embodied to record X-ray projections of a region of interest comprising a parameter-adjusting unit according to at least one embodiment of the invention.

At least one embodiment of the invention furthermore relates to a fluoroscopy unit or an angiography unit comprising a parameter-adjusting unit according to at least one embodiment of the invention or an X-ray unit according to at least one embodiment of the invention. A fluoroscopy unit or an angiography unit can in particular be a C-arm X-ray device or a computed tomography scanner.

At least one embodiment of the invention also relates to a computer program product with a computer program and/or a computer-readable medium. An extensively software-based implementation has the advantage that it is also possible to retrofit parameter-adjusting units used to date in a simple way via a software update in order to work in the manner according to at least one embodiment of the invention. In addition to the computer program, a computer program product of this kind can optionally comprise additional constituents such as, for example, documentation and/or additional components and also hardware components, such as, for example hardware keys (dongles etc.) for using the software.

BRIEF DESCRIPTION OF THE DRAWINGS

The following describes and explains the invention is more detail with reference to the example embodiments depicted in the figures, which show.

DETAILED DESCRIPTION OF THE EXAMPLE EMBODIMENTS

Figure 1:
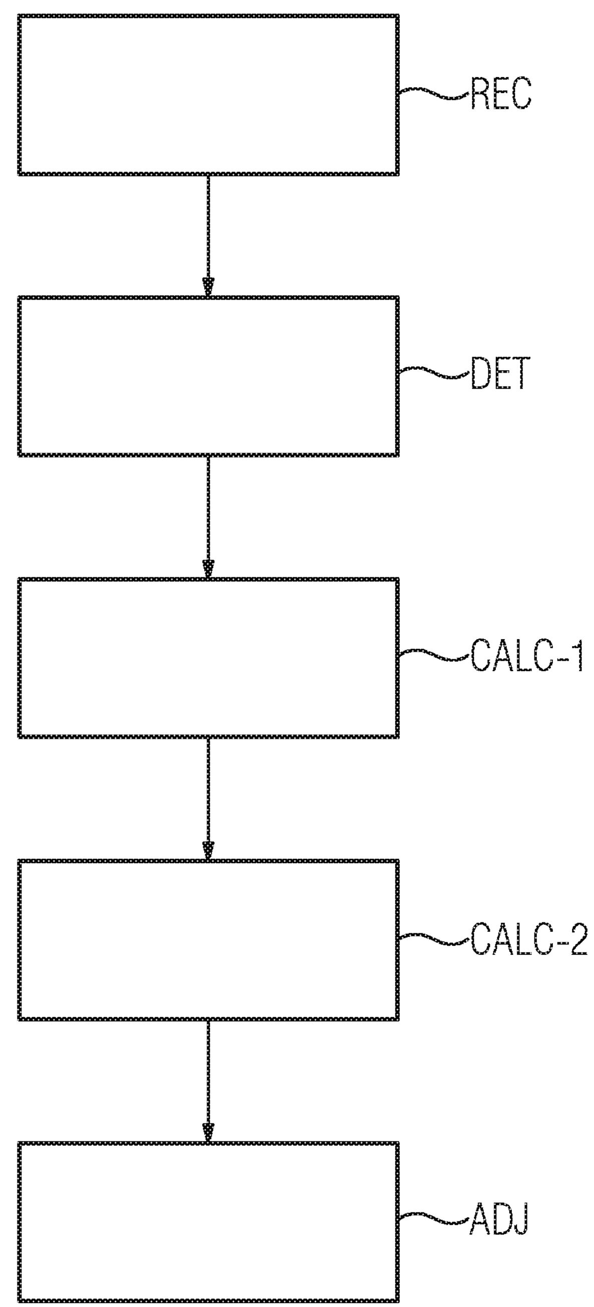
FIG. 1 is a flow diagram of an embodiment of the method.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or porcessors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (procesor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the invention is based on the fact that an X-ray projection of a region of interest and an associated X-ray parameter is received via an interface, wherein the X-ray projection comprises X-ray intensities in a first pixel set and wherein the X-ray parameter relates to at least one X-ray voltage from an X-ray source. At least one embodiment of the invention is furthermore based on the fact that scattered radiation intensities are determined in a second pixel set via a computing unit, wherein the second pixel set is a subset of the first pixel set. Furthermore, there is a first calculation of first exposure parameters in the second pixel set, wherein each of the first exposure parameters in a pixel of the second pixel set is based on the X-ray intensity in the pixel and the scattered radiation intensity in the pixel. Furthermore, there is a second calculation of a scalar second exposure parameter based on the first exposure parameters and an adjustment of the X-ray parameter by comparing the scalar second exposure parameter with a reference value. A first pixel set is in particular a non-empty set of pixels, a second pixel set is in particular a non-empty set of pixels.

The inventors have identified that the X-ray parameter, in particular the X-ray intensity, can be adjusted particularly quickly and simply based on a scalar second exposure parameter and simultaneously, since the scattered radiation intensity is taken into account in the first calculation of the first exposure parameters, the quantitative influences of the scattered radiation on the generated X-ray image data are also included in the adjustment of the X-ray parameter. Furthermore, the comparison of the scalar second exposure parameter with only one reference value can take place very quickly. Furthermore, the use of a scalar second exposure parameter enables the parameters of homogeneous X-ray sources to be adjusted particularly efficiently.

According to a further embodiment of the invention, each of the first exposure parameters corresponds to a primary radiation intensity, wherein the primary radiation intensity in a pixel of the second pixel set is the difference between the X-ray intensity in the pixel and the scattered radiation intensity in the pixel. The inventors have identified that the primary radiation intensity is a suitable exposure parameter for the adjustment of the X-ray parameter. For example, the adjustment can take place such that a minimum primary radiation intensity required for imaging can be achieved in a pixel.

According to a further embodiment of the invention, each of the first exposure parameters in a pixel of the second pixel set corresponds to the ratio of the primary radiation intensity in the pixel to the scattered radiation intensity in the pixel. A first exposure parameter can then in particular be a signal-noise ratio (an English technical term). The inventors have identified that the signal-noise ratio is a particularly good indicator of the quality of the X-ray image and therefore the X-ray parameter can be adjusted particularly simply and efficiently based on the signal-noise ratio.

According to a further embodiment of the invention, the scalar second exposure parameter is determined by averaging the first exposure parameters of a third pixel set, wherein the second pixel set comprises the third pixel set. The inventors have identified that averaging is a very quick and efficient method for generating a scalar second exposure parameter from a plurality of first exposure parameters.

According to a further embodiment of the invention, the scalar second exposure parameter is a quantile of a distribution of the first exposure parameters in a third pixel set, wherein the second pixel set comprises the third pixel set. The inventors have identified that the use of a quantile causes outliers in the set of the first exposure parameters to have at the most a small influence on the scalar second exposure parameter and, therefore, the use of such a scalar second exposure parameter in particular has little susceptibility to errors.

According to a further embodiment of the invention, furthermore an anatomical parameter of the region of interest is received and the determination of the scattered radiation intensities takes place by retrieving a reference dataset from a reference database, wherein the reference dataset is selected using a comparison with the anatomical parameter and the X-ray parameter. The reference dataset in particular comprises a reference scattered radiation intensity. The inventors have identified that the use of a reference dataset means there is no need for time-consuming or expensive measurement or determination of the scattered radiation intensity and hence the method can be performed quickly and cost-effectively.

According to a further embodiment of the invention, furthermore an anatomical parameter of the region of interest is received and the determination of the scattered radiation intensity takes place by way of a Monte-Carlo simulation using the anatomical parameter and the X-ray parameter. The inventors have identified that a Monte-Carlo simulation taking account of the anatomical parameter enables the scattered radiation intensity to be determined particularly accurately and hence the method has little susceptibility to errors.

According to a further embodiment of the invention, the anatomical parameter at least comprises the extension of the region of interest with respect to the direction of projection of the X-ray projection. The inventors have identified that the scattered radiation intensity is particularly influenced by the extension of the region of interest and hence the choice of this extension as an anatomical parameter enables scattered radiation intensity to be determined particularly efficiently and simultaneously quickly.

According to a further embodiment of the invention, the anatomical parameter comprises a three-dimensional model of the region of interest, wherein the three-dimensional model is determined by way of the X-ray image dataset. The inventors have identified that a three-dimensional model enables the scattered radiation distribution to be determined particularly accurately.

According to a further embodiment of the invention, the determination takes place by measuring the scattered radiation intensities. The inventors have identified that a measurement of the scattered radiation intensities is not dependent on model assumptions and consequently the scattered radiation intensity can be calculated without model-induced errors and therefore particularly accurately.

According to a further embodiment of the invention, the measurement of the scattered radiation intensities takes place by the introduction of an X-ray-absorbing object into the beam path between the X-ray source and the region of interest, wherein the X-ray-absorbing object absorbs at least 90% or at least 95% or at least 99% of the incident X-rays and wherein the scattered radiation intensities correspond to the X-ray intensities in the shadow pixels of the image of the X-ray-absorbing object in the X-ray projection. The inventors have identified that such screening of the primary radiation enables the scattered radiation to be determined particularly simply and quickly as X-ray intensity in the X-ray shadow of the X-ray-absorbing object.

At least one embodiment of the invention furthermore relates to a parameter-adjusting unit for adjusting an X-ray parameter of an X-ray unit, wherein the X-ray unit comprises an X-ray source and an X-ray detector comprising the following units:

an interface embodied for the reception of an X-ray projection of a region of interest and an associated X-ray parameter, wherein the X-ray projection comprises X-ray intensities in a first pixel set and wherein the X-ray parameter relates to at least one X-ray voltage from the X-ray source, a computing unit embodied for the determination of scattered radiation intensities in a second pixel set, wherein the second pixel set is a subset of the first pixel set, furthermore embodied for the first calculation of first exposure parameters in the second pixel set, wherein each of the first exposure parameters in a pixel of the second pixel set is based on the X-ray intensity in the pixel and the scattered radiation intensity in the pixel, furthermore embodied for the second calculation of a scalar second exposure parameter based on the first exposure parameters, furthermore embodied for the adjustment of the X-ray parameter by comparing the scalar second exposure parameter with a reference value.

Such a parameter-adjusting unit can in particular be embodied to carry out embodiments of the inventive methods described. The parameter-adjusting unit is embodied to carry out these methods and the embodiments thereof in that the interface and the computing unit are embodied to carry out the corresponding method steps.

At least one embodiment of the invention furthermore relates an X-ray unit embodied to record X-ray projections of a region of interest comprising a parameter-adjusting unit according to at least one embodiment of the invention.

At least one embodiment of the invention furthermore relates to a fluoroscopy unit or an angiography unit comprising a parameter-adjusting unit according to at least one embodiment of the invention or an X-ray unit according to at least one embodiment of the invention. A fluoroscopy unit or an angiography unit can in particular be a C-arm X-ray device or a computed tomography scanner.

At least one embodiment of the invention also relates to a computer program product with a computer program and/or a computer-readable medium. An extensively software-based implementation has the advantage that it is also possible to retrofit parameter-adjusting units used to date in a simple way via a software update in order to work in the manner according to at least one embodiment of the invention. In addition to the computer program, a computer program product of this kind can optionally comprise additional constituents such as, for example, documentation and/or additional components and also hardware components, such as, for example hardware keys (dongles etc.) for using the software.

An X-ray projection is a depiction of a three-dimensional region of interest in a two-dimensional image, in particular in a flat image, by way of X-rays. Herein X-rays in particular denote electromagnetic rays with a wavelength of between 1 picometer and 250 picometers, in particular with a wavelength of between 1 picometer and 60 picometers. The X-rays are emitted by an X-ray source and detected by an X-ray detector. Herein, the intensity of the X-rays in the X-ray detector is inter alia dependent upon the material distribution and the material properties in the region of interest.

An X-ray projection can comprise a set of X-ray intensity values, in particular a set of pixels or a pixel set, wherein an X-ray intensity is in each case assigned to each pixel. Herein, the X-ray intensity in a pixel is the intensity of the X-rays arriving at this pixel. The X-ray intensity is made up of the primary radiation intensity and the scattered radiation intensity, wherein the primary radiation intensity is the intensity of the unscattered X-rays and wherein the scattered radiation intensity is the intensity of the scattered X-rays at at least one scatter center. Herein, an X-ray detector is not able to differentiate between primary radiation and scattered radiation but is only able to measure a summated X-ray intensity.

An X-ray parameter denotes a parameter affecting an X-ray projection that can be adjusted at the X-ray source or at the X-ray detector. Examples of an X-ray parameter are the X-ray voltage or X-ray current of the X-ray source, in particular an X-ray tube, or the duration of the exposure of the region of interest to the X-rays.

An exposure parameter is in particular a measure of the image quality, in particular the contrast or the noise in a part of the X-ray projection, in particular in a pixel of the X-ray projection. Herein an exposure parameter can be assigned to each pixel in a pixel set. A scalar exposure parameter is in particular a number with or without a unit obtained from the exposure parameters of a plurality of regions, in particular a plurality of pixels of the X-ray projection.

One anatomical parameter of the region of interest describes the anatomy of the region of interest. It can in particular relate to the extension of the region of interest in one or more directions or depict the outer geometric shape of the region of interest. Furthermore, it can also depict the internal structure of the region of interest; in particular, the anatomical parameter can also be a three-dimensional model or a three-dimensional depiction of the region of interest.

FIG. 1 is a flow diagram of an example embodiment of the method for adjusting an X-ray parameter of an X-ray unit 300, wherein the X-ray unit 300 comprises an X-ray source 301 and an X-ray detector 302.

The first step of the example embodiment depicted is the reception REC of an X-ray projection of a region of interest 303 and an associated X-ray parameter via an interface 201, wherein the X-ray projection comprises X-ray intensities 400 in a first pixel set and wherein the X-ray parameter relates to at least one X-ray voltage from the X-ray source 301. In the region of implementation depicted, the region of interest 303 is a patient's thorax, but other body regions or parts of other objects are possible as regions of interest 303. In the example embodiment depicted, the X-ray projection was recorded with an X-ray detector 303, in the example embodiment depicted, the first pixel set corresponds to all pixels in the X-ray projection, however, it is also possible to use only a part of the pixels of the X-ray projection. In the example embodiment shown, the X-ray parameter is identical to the X-ray voltage of the X-ray tube 301, however, it is also possible to incorporate other parameters in the method, for example the X-ray current. Furthermore, in the example embodiment depicted, an anatomical parameter of the region of interest 303 is received, wherein, in this example embodiment, the anatomical parameter is the extension of the region of interest 303 in the direction of projection Z of the X-ray projection.

In the example embodiment depicted, the next step is the determination DET of scattered radiation intensities 402 in a second pixel set via a computing unit 202, wherein the second pixel set is a subset of the first pixel set. In the example embodiment depicted, the anatomical parameter and the X-ray voltage are used to retrieve a reference dataset comprising a reference scattered radiation intensity from a database 206. Herein, the reference scattered radiation intensity corresponds to the scattered radiation intensity 402 of an X-ray recording of a reference region of interest, with a reference extension in the direction of projection Z using a reference X-ray voltage. The reference dataset is selected such that the standardized reference extension and the standardized extension of the region of interest 303 and the standardized reference X-ray parameter and the standardized X-ray parameter are as similar as possible, in particular the difference between them is as little as possible. Herein, the reference extension and the extension of the region of interest 303 are standardized to the bandwidth of the reference extensions in the database 206 and the X-ray voltage and the reference X-ray voltage standardized to the bandwidth of the reference X-ray voltages in the database 206. Herein, in this example embodiment, the standardized reference extension and the standardized extension of the region of interest 303 and the standardized reference X-ray parameter and the standardized X-ray parameter are as similar as possible if the sum of the squared deviation of the standardized reference extension from the standardized extension of the region of interest 303 and the squared deviation of the standardized reference X-ray parameter from the standardized X-ray parameter is minimal compared to the other reference datasets. It is also possible to weight one of the squared deviations more highly or to use other distancing terms.

Alternatively, the determination DET of the scattered radiation intensity 402 can also take place by way of a Monte-Carlo simulation. Herein, an anatomical parameter (for example the extension of the region of interest 303 in the direction of projection Z) and the X-ray projection are used to determine a three-dimensional model of the region of interest 303. Herein, the three-dimensional model relates to at least one three-dimensional distribution of an X-ray absorption coefficient. The determination of the three-dimensional model can, for example, take place by way of a comparison with reference models in a database 206, which was obtained with three-dimensional imaging, for example via a computed tomography scanner. The three-dimensional model can also take place by way of the adjustment of a suitable standard model to the anatomical parameter and the X-ray projection. Furthermore, the three-dimensional model can also be obtained from a previous imaging examination of the same region of interest.

In a Monte-Carlo simulation, the paths are simulated by individual X-ray photons from the X-ray source 301. Herein, an initial direction and an initial energy of an X-ray photon is randomly determined from the directional and energy distribution of the X-ray source 301.

For an X-ray photon with direction and energy, it is possible to determine a distribution of path lengths, wherein a path length is the length between two interactions and wherein the distribution of the path length is dependent upon the energy of the X-ray photon and the X-ray absorption coefficient of the region of the three-dimensional model which is passed through. A path length is selected randomly in accordance with the distribution of the path lengths. If the X-ray photon arrives at the X-ray detector 302 within the path length, it is registered in the X-ray detector 302. If this not the case, an interaction event takes place at a scatter center 306 in the simulation after the path length. The type of interaction (absorption, Compton scattering or Thomson scattering) is determined randomly using the respective effective cross section; the energy and direction of the X-ray photon after the interaction is also obtained randomly from the distributions of the respective interaction process, which depend at least upon the energy of the X-ray photon before the interaction. This process is repeated until the X-ray photon has been absorbed in the X-ray detector 302 or in the region of interest 303 or leaves the simulated region. Herein, an X-ray photon is registered in the X-ray detector 302 as a scattered radiation photon if it has participated in an interaction; otherwise, it is registered as a primary radiation photon.

In a further alternative, the determination DET of the scattered radiation intensity 402 can also take place via a direct measurement. To this end, an X-ray absorbing object 500 is introduced into the beam path between the X-ray source 301 and the region of interest 303, wherein the X-ray-absorbing object 500 attenuates, for example, 99% of the incident X-ray intensity 400. The X-ray-absorbing object 500 generates an X-ray shadow 501 on one or more shadow pixels 502.1, . . . , 502.4 of the X-ray detector 302 and so only secondary radiation 305 arrives in the shadow pixels 502.1, . . . , 502.4.

Therefore, the X-ray intensity 400 in the shadow pixels 502.1, . . . , 502.4 substantially corresponds to the scattered radiation intensity 402 in shadow pixels 502.1, . . . , 502.4. The second pixel set can be identical to the shadow pixels; due to the low dynamics of the scattered radiation intensity 402, it is possible to draw conclusions regarding the scattered radiation intensity 402 in a larger second pixel set or alternatively in the entire image, for example in that a constant scattered radiation intensity 402 is assumed for the entire image. It is also possible to move the X-ray-absorbing object 500 in the beam path in order to measure the scattered radiation intensity 402 in a plurality of regions or to use a plurality of X-ray-absorbing objects 500. If the X-ray-absorbing object 500 is placed on the edge of the beam path, it can also remain in the beam path during the recording of further X-ray projections with a changed X-ray parameter.

A further step of the example embodiment is the first calculation CALC-1 of first exposure parameters in the second pixel set via the computing unit 202, wherein each of the first exposure parameters in a pixel of the second pixel set is based on the X-ray intensity 400 in the pixel and the scattered radiation intensity 402 in the pixel. In the example embodiment depicted, a first exposure parameter in a pixel corresponds to the ratio of the primary radiation intensity 401 to the scattered radiation intensity 402 in the respective pixel, i.e. to a signal-noise ratio. However, it is also possible to use the primary radiation intensity 401 directly as a first exposure parameter or other exposure parameters. Herein, the primary radiation intensity 401 can be calculated as the difference between the X-ray intensity 400 and the scattered radiation intensity 402 determined in the preceding step of the method.

In the next step of the example embodiment, a second calculation CALC-2 of a scalar second exposure parameter takes place based on the first exposure parameters via the computing unit 202. In the example embodiment depicted, the scalar second exposure parameter is the mean value of the first exposure parameters of the second pixel set. However, it is also conceivable to use the median or another quantile of the distribution of the first exposure parameters of the second pixel set. It is furthermore possible to use the smallest of the first exposure parameters or the largest of the first exposure parameters of the second pixel set as a scalar second exposure parameter.

The last step of the example embodiment is the adjustment ADJ of the X-ray parameter by comparing the scalar second exposure parameter with a reference value via the computing unit 202. In the example embodiment depicted, the X-ray parameter corresponds to the X-ray voltage from the X-ray source 301 and the scalar second exposure parameter corresponds to the mean value of the signal-noise ratio. In the example embodiment depicted, the X-ray voltage is increased by a previously defined difference if the mean value of the signal-noise ratio is below the reference value and the X-ray voltage is reduced by a previously defined difference if the mean value of the signal-noise ratio is above the reference value. However, it is also possible to use the mean value of the signal-noise ratio as the actual value and the reference value as the reference value for a control process, in particular of a proportional controller, an integral controller or a differential controller or a combination of these three controllers (an acronym for the combination is "PID controller").

In the example embodiment depicted, the adjustment ADJ of the X-ray parameter takes place using the received X-ray projection. The adjusted X-ray parameter is then used to record all further X-ray projections required for an examination. However, it is also possible to carry out the method several times during the examination, in particular to apply the method to each of the X-ray projections recorded during the examination in order to achieve a better, in particular continuous adjustment of the X-ray parameter. This in particular enables account to be taken of changes to the region of interest in the readjustment of the X-ray parameter. It is furthermore in particular possible to perform the method several times during the examination for a fluoroscopy examination or for an angiography examination, in particular to apply the method to each of the X-ray projections recorded during the examination.

Figure 2:
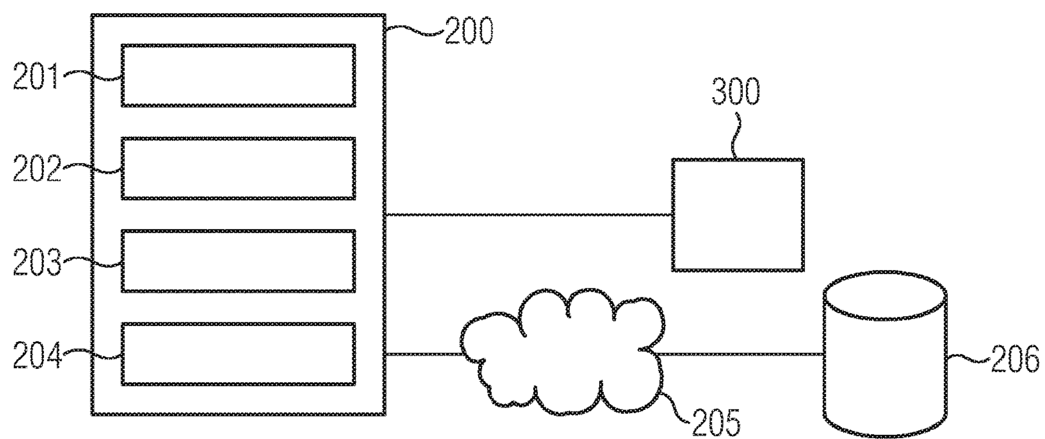
FIG. 2 is an embodiment of a parameter-adjusting unit.

FIG. 2 shows a parameter-adjusting unit 200 for the adjustment of an X-ray parameter. The parameter-adjusting unit 200 shown here is configured to carry out a method according to the invention. This parameter-adjusting unit 200 comprises an interface 201, a computing unit 202, a storage unit 203 and an input and output unit 204.

The parameter-adjusting unit 200 can in particular be a computer, a microcontroller or an integrated circuit. Alternatively, the parameter-adjusting unit 200 can be a real or virtual group of computers (an English technical term for a real group is "cluster", a English technical term for a virtual group is "cloud"). An interface 201 can be a hardware or software interface (for example, PCI-Bus, USB or Firewire). A computing unit 202 can comprise a hardware element or software elements, for example a microprocessor or a so-called FPGA (English abbreviation for "field programmable gate array"). A storage unit 203 can be embodied as a non-permanent main memory (random access memory, RAM for short) or as a permanent mass storage device (hard disk, USB stick, SD card, solid state disk). An input and output unit 204 comprises at least one input unit and/or at least one output unit.

In the example embodiment depicted, the parameter-adjusting unit 200 is connected to a database 206 via a network 205. The database 205 comprises reference datasets comprising an anatomical reference parameter, a reference X-ray parameter and a reference scattered radiation intensity. The network 205 can, for example, be embodied as a local intranet or as the internet. Alternatively, it is also possible for the database 206 to be embodied directly in the storage unit 203 of the parameter-adjusting unit 200. In this case, a connection via a network 205 is not necessary.

Figure 3:
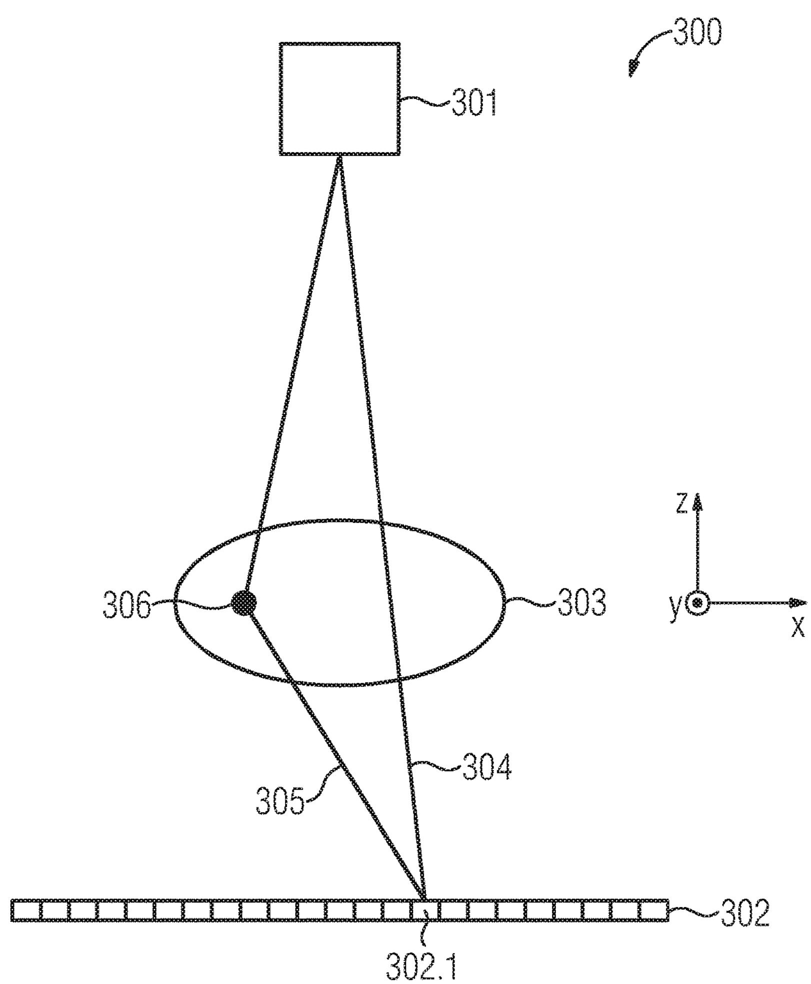
FIG. 3 is an embodiment of an X-ray unit.

FIG. 3 shows an X-ray unit 300 comprising an X-ray source 301 and an X-ray detector 302 embodied to record X-ray projections of a region of interest 303. In the example embodiment depicted, the X-ray unit 300 is a component of a C-arm X-ray device (not depicted), with which the radiographic, angiographic or fluoroscopic images can be recorded. However, the X-ray unit 300 can also be part of other X-ray devices, in particular, the X-ray unit 300 can also be part of a computed tomography scanner.

In the example embodiment depicted, the X-ray source 301 is an X-ray tube. However, it is also possible for the X-ray source 301 to be embodied in another way for example as a linear accelerator (an English technical term, "LINAC" for short), as a synchrotron or as a X-ray laser. In the example embodiment depicted, the X-ray detector 302 is a digital full-field detector. However, it is also possible to use other X-ray detectors 302 such as, for example, solid-state detectors.

The X-ray source 301 emits X-rays 304, 305 along a direction of projection Z. Herein, the X-rays 304, 305 are registered in pixels 302.1 of the X-ray detector 302. Herein, with X-rays, a distinction can be made between primary radiation 304 and scattered radiation 305. Primary radiation 304 is not scattered, but only attenuated between the X-ray source 301 and the X-ray detector 302, in particular in the region of interest 303. Herein, a attenuation of the primary radiation 304 causes a decrease in the X-ray intensity 400 in the X-ray detector 302. In particular, the primary radiation 304 extends on a straight line between the X-ray detector 302 and the registering pixel 302.1 of the X-ray detector 302.

Scattered radiation 305 is scattered between the X-ray source 301 and the X-ray detector 302, in particular in the region of interest 303 at a scatter center 306. Herein, the scattering of the X-ray photons takes place in the typical parameter range of medical applications with a probability of more than 90% with Compton scattering (interaction with a weakly bound electron of the electron shell of an atom with X-ray photon energy loss) and of less than 10% with Thomson scattering (scattering on a core charge or on an electron of the electron shell of an atom without X-ray photon energy loss). The scattering causes the X-ray photons to change direction and hence to lose their directional information.

With an X-ray detector 302, it is not possible to differentiate between primary radiation 304 and scattered radiation 305 and therefore an X-ray detector 302 can generally only measure the entire X-ray intensity 400, but not the primary radiation intensity 401 and scattered radiation intensity 402 separately. To minimize the scattered radiation intensity 402, it is possible to take special measures, for example by direction-sensitive scattered radiation grids, which are not shown in FIG. 3 for purposes of clarity.

Figure 4:
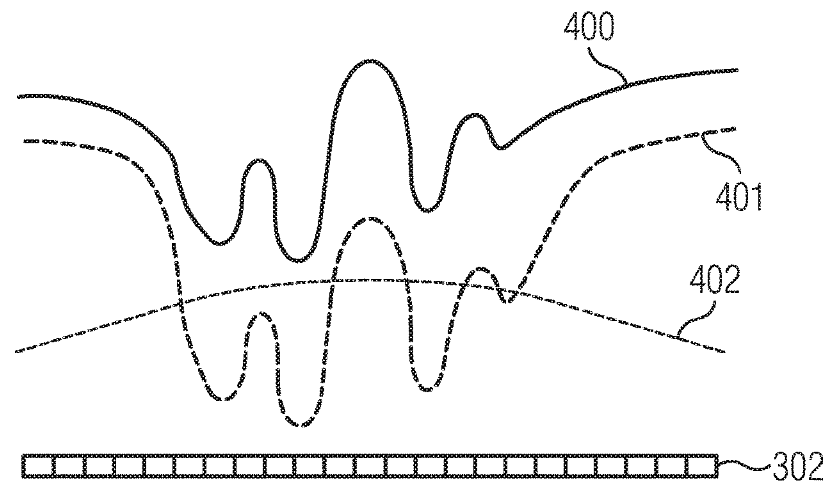
FIG. 4 is an embodiment of a primary radiation distribution, a scattered radiation distribution and a total radiation intensity distribution.

FIG. 4 shows a spatially resolved X-ray intensity 400 in an X-ray detector 302 with a medical X-ray recording obtained from the addition of a spatially resolved primary radiation intensity 401 and a spatially resolved scattered radiation intensity 402. Herein, the primary radiation intensity 401 has high dynamics due to different X-ray absorption rates in the region of interest 303, while the scattered radiation intensity 402 has low dynamics and only drops to the edges of the detector.

The high dynamics of the primary radiation intensity 401 results from the high dynamics of the X-ray absorption in the region of interest 303 where, for example, bones have high degree of X-ray absorption and soft-tissue has a low degree of X-ray absorption.

The low dynamics of the scattered radiation intensity 402 results from the fact that the angular distribution 305 is virtually homogeneous for both Compton scattering and Thomson scattering for forward scattering in the direction of the X-ray detector 302. The subsequent drop at the edges of the scattered radiation intensity 402 is due to fact that, with pixels at the edge of the X-ray detector 302, scattered radiation 305 with scatter centers 306 is only registered from a smaller angular range than with pixels in the center of the X-ray detector 302.

Figure 5:
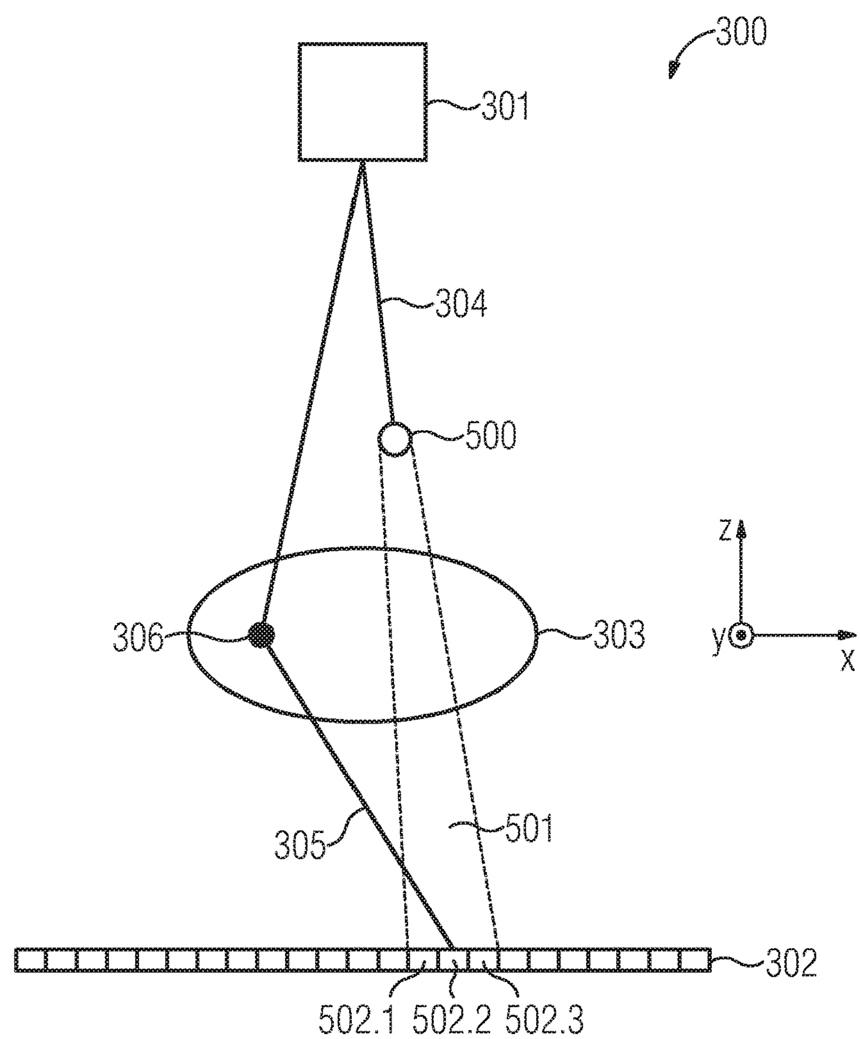
FIG. 5 is an embodiment of an X-ray unit with an X-ray-absorbing object.

FIG. 5 shows an X-ray unit 300 with an X-ray-absorbing object 500 in the beam path between the X-ray source 301 and the region of interest 303. In the example embodiment shown, the X-ray-absorbing object 500 absorbs more than 99% of the X-ray intensity 400 and hence generates an X-ray shadow 501 on shadow pixels 502.1, . . . , 502.4 of the X-ray detector 302. Therefore, substantially only scattered radiation 305 can now arrive at the shadow pixels 502.1, . . . , 502.4. Therefore, the X-ray intensity 400 measured in the shadow pixels 502.1, . . . , 502.4 is substantially the same as the scattered radiation intensity 402. If the X-ray-absorbing object 500 is removed from the beam path, the X-ray intensity 400 measured in the shadow pixels 502.1, . . . , 502.4 is again the sum of the primary radiation intensity 401 and the scattered radiation intensity 402. Therefore, a comparison of the X-ray intensity 400 with the presence of the X-ray-absorbing object 500 and the X-ray intensity 400 without the presence of the X-ray-absorbing object 500 enables conclusions to be drawn regarding the primary radiation intensity 401. Furthermore, it is also possible for the scattered radiation intensity 402 to be extrapolated to larger pixel sets.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase “means for” or, in the case of a method claim, using the phrases “operation for” or “step for.”

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for adjusting an X-ray parameter of an X-ray unit, the X-ray unit including an X-ray source and an X-ray detector, the method comprising:

receiving, via an interface, an X-ray projection of a region of interest and an associated X-ray parameter, the X-ray projection including X-ray intensities in a first pixel set and the X-ray parameter relating to at least one X-ray voltage from the X-ray source;

determining scattered radiation intensities in a second pixel set via a computing unit, the second pixel set being a subset of the first pixel set;

calculating, via the computing unit, first exposure parameters in the second pixel set, each of the first exposure parameters in a pixel of the second pixel set being respectively based on the X-ray intensity in the respective pixel and the scattered radiation intensity in the respective pixel;

calculating, via the computing unit, a scalar second exposure parameter based on the first exposure parameters; and adjusting the X-ray parameter by comparing, via the computing unit, the scalar second exposure parameter with a reference value.

2. The method of claim 1, wherein each of the first exposure parameters corresponds to a primary radiation intensity and wherein the respective primary radiation intensity in a respective pixel of the second pixel set is a difference between the X-ray intensity in the respective pixel and the scattered radiation intensity in the respective pixel.

3. The method of claim 1, wherein each of the first exposure parameters in a respective pixel of the second pixel set corresponds to a ratio of the primary radiation intensity in the respective pixel to the scattered radiation intensity in the respective pixel.

4. The method of claim 1, wherein the determining of the scalar second exposure parameter includes averaging the first exposure parameters of a third pixel set, the second pixel set including the third pixel set.

5. The method of claim 1, wherein the scalar second exposure parameter is a quantile of a distribution of the first exposure parameters in a third pixel set, the second pixel set including the third pixel set.

6. The method of claim 1, further comprising:

receiving an anatomical parameter of the region of interest, wherein the determining of the scattered radiation intensities includes retrieving a reference dataset from a reference database, the reference dataset being selected using a comparison with the anatomical parameter and the X-ray parameter.

7. The method of claim 1, further comprising:

receiving an anatomical parameter of the region of interest, wherein the determining of the scattered radiation intensity takes place by way of a Monte-Carlo simulation using the anatomical parameter and the X-ray parameter.

8. The method of claim 6, wherein the anatomical parameter includes an extension of the region of interest with respect to a direction of projection of the X-ray projection.

9. The method of claim 6, wherein the anatomical parameter includes a three-dimensional model of the region of interest and wherein the three-dimensional model is determined by way of the X-ray image dataset.

10. The method of claim 1, wherein the determining takes place by measuring the scattered radiation intensities.

11. The method of claim 10, wherein the measuring of the scattered radiation intensities takes place by introducing an X-ray-absorbing object in a beam path between the X-ray source and the region of interest, wherein the X-ray-absorbing object absorbs at least 90% of the incident X-rays, and wherein the scattered radiation intensities correspond to the X-ray intensities in the shadow pixels of the image of the X-ray-absorbing object in the X-ray projection.

12. A parameter-adjusting unit for adjusting an X-ray parameter of an X-ray unit, the X-ray unit including an X-ray source and an X-ray detector, parameter-adjusting unit comprising:

an interface, configured to receive an X-ray projection of a region of interest and an associated X-ray parameter, the X-ray projection including X-ray intensities in a first pixel set and the X-ray parameter relating to at least one X-ray voltage from the X-ray source; and a computing unit, configured to determine scattered radiation intensities in a second pixel set, the second pixel set being a subset of the first pixel set, calculate first exposure parameters in the second pixel set, each of the respective first exposure parameters in a respective pixel of the second pixel set being based on the X-ray intensity in the respective pixel and the scattered radiation intensity in the respective pixel, calculate a scalar second exposure parameter based on the first exposure parameters, and adjust the X-ray parameter by comparing the scalar second exposure parameter with a reference value.

13. The parameter-adjusting unit of claim 12, wherein each of the first exposure parameters corresponds to a primary radiation intensity and wherein the respective primary radiation intensity in a respective pixel of the second pixel set is a difference between the X-ray intensity in the respective pixel and the scattered radiation intensity in the respective pixel.

14. An X-ray unit configured to record X-ray projections of a region of interest, comprising the parameter-adjusting unit of claim 12.

15. A non-transitory computer program product including a computer program, directly loadable into a memory unit of a parameter-adjusting unit, the computer program including program sections to carry out the method of claim 1 when the program sections are executed by the parameter-adjusting unit.

16. A non-transitory computer-readable storage medium including program sections, readable and executable by a parameter-adjusting unit, stored to carry out the method of claim 1 when the program sections are executed by the parameter-adjusting unit.

17. The method of claim 2, wherein the determining of the scalar second exposure parameter includes averaging the first exposure parameters of a third pixel set, the second pixel set including the third pixel set.

18. The method of claim 3, wherein the determining of the scalar second exposure parameter includes averaging the first exposure parameters of a third pixel set, the second pixel set including the third pixel set.

19. The method of claim 2, wherein the scalar second exposure parameter is a quantile of a distribution of the first exposure parameters in a third pixel set, the second pixel set including the third pixel set.

20. The method of claim 3, wherein the scalar second exposure parameter is a quantile of a distribution of the first exposure parameters in a third pixel set, the second pixel set including the third pixel set.

21. The method of claim 7, wherein the anatomical parameter includes an extension of the region of interest with respect to a direction of projection of the X-ray projection.

22. The method of claim 7, wherein the anatomical parameter includes a three-dimensional model of the region of interest and wherein the three-dimensional model is determined by way of the X-ray image dataset.

23. An X-ray unit configured to record X-ray projections of a region of interest, comprising the parameter-adjusting unit of claim 13.

24. A non-transitory computer-readable storage medium including program sections, readable and executable by a parameter-adjusting unit, stored to carry out the method of claim 2 when the program sections are executed by the parameter-adjusting unit.

* * * * *